(12) United States Patent
Devore et al.

(10) Patent No.: US 7,651,683 B2
(45) Date of Patent: Jan. 26, 2010

(54) POLYMERIZABLE EMULSIONS FOR TISSUE ENGINEERING

(75) Inventors: David Devore, Princeton, NJ (US); Paul Ducheyne, Rosemont, PA (US); Charles Cohen, Gladwyne, PA (US)

(73) Assignee: Gentis, Inc., Philadelphia, PA (US)

( * ) Notice: Subject to any disclaimer, the term of this patent is extended or adjusted under 35 U.S.C. 154(b) by 0 days.

(21) Appl. No.: 11/799,347

(22) Filed: May 1, 2007

(65) Prior Publication Data

US 2007/0218124 A1 Sep. 20, 2007

Related U.S. Application Data

(62) Division of application No. 10/977,521, filed on Oct. 29, 2004.

(60) Provisional application No. 60/515,404, filed on Oct. 29, 2003.

(51) Int. Cl.
*A61K 31/74* (2006.01)
*A61K 6/083* (2006.01)
*A61F 2/00* (2006.01)

(52) U.S. Cl. ............... 424/78.08; 424/78.31; 523/105; 523/113

(58) Field of Classification Search ............... None
See application file for complete search history.

(56) References Cited

U.S. PATENT DOCUMENTS

| | | | |
|---|---|---|---|
| 3,900,559 A * | 8/1975 | Sim et al. ............... 514/454 |
| 3,961,379 A | 6/1976 | Highgate et al. |
| 4,408,028 A | 10/1983 | Nakayama et al. |
| 4,522,961 A * | 6/1985 | Martino et al. ............... 523/407 |
| 4,702,997 A | 10/1987 | Ai et al. |
| 4,772,287 A | 9/1988 | Ray |
| 4,904,260 A | 2/1990 | Ray |
| 5,008,303 A * | 4/1991 | Gasser et al. ............... 522/64 |
| 5,047,055 A | 9/1991 | Bao |
| 5,108,438 A | 4/1992 | Stone |
| 5,145,675 A * | 9/1992 | Won ............... 424/78.31 |
| 5,151,217 A | 9/1992 | Price |
| 5,192,326 A | 3/1993 | Bao |
| 5,204,106 A | 4/1993 | Schepers |
| 5,258,028 A * | 11/1993 | Ersek et al. ............... 623/23.73 |
| 5,258,043 A | 11/1993 | Stone |
| 5,405,618 A * | 4/1995 | Buttery et al. ............... 424/486 |
| 5,500,451 A * | 3/1996 | Goldman et al. ............... 521/64 |
| 5,674,295 A | 10/1997 | Ray |
| 5,681,872 A * | 10/1997 | Erbe ............... 523/114 |
| 5,723,512 A * | 3/1998 | Leppard et al. ............... 522/55 |
| 5,753,359 A * | 5/1998 | Dyer et al. ............... 428/315.5 |
| 5,888,220 A | 3/1999 | Felt |
| 5,914,356 A * | 6/1999 | Erbe ............... 523/114 |
| 5,964,807 A | 10/1999 | Gan |
| 6,013,853 A * | 1/2000 | Athanasiou et al. ............... 424/423 |
| 6,045,972 A | 4/2000 | Salvin |
| 6,103,255 A * | 8/2000 | Levene et al. ............... 424/426 |
| 6,143,293 A * | 11/2000 | Weiss et al. ............... 424/93.7 |
| 6,187,048 B1 * | 2/2001 | Milner et al. ............... 623/17.12 |
| 6,849,092 B2 | 3/2001 | VanDyke |
| 6,224,630 B1 | 5/2001 | Bac et al. |
| 6,224,893 B1 * | 5/2001 | Langer et al. ............... 424/423 |
| 6,228,900 B1 * | 5/2001 | Shen et al. ............... 522/153 |
| 6,231,714 B1 * | 5/2001 | Woods et al. ............... 156/275.7 |
| 6,240,926 B1 | 6/2001 | Gan et al. |
| 6,607,558 B2 | 7/2001 | Kuras |
| 6,298,189 B1 | 10/2001 | Szum et al. |
| 6,328,990 B1 | 12/2001 | Ducheyne et al. |
| 6,337,198 B1 * | 1/2002 | Levene et al. ............... 435/174 |
| 6,346,123 B1 | 2/2002 | McKay et al. |
| 6,376,742 B1 * | 4/2002 | Zdrahala et al. ............... 623/11.11 |
| 6,395,029 B1 * | 5/2002 | Levy ............... 623/11.11 |
| 6,414,086 B1 | 7/2002 | Wang et al. |
| 6,423,333 B1 | 7/2002 | Stedronsky |
| 6,428,576 B1 | 8/2002 | Haldimann |
| 6,436,137 B2 | 8/2002 | Wang et al. |
| 6,436,426 B1 * | 8/2002 | Liao et al. ............... 424/426 |
| 6,503,958 B2 | 8/2002 | Hughes et al. |
| 6,444,725 B1 | 9/2002 | Trom et al. |
| 6,462,109 B1 * | 10/2002 | Sharma et al. ............... 523/501 |
| 6,471,993 B1 * | 10/2002 | Shastri et al. ............... 424/486 |
| 6,482,235 B1 | 11/2002 | Lambrecht et al. |
| 6,497,729 B1 | 12/2002 | Moussy et al. |
| 6,514,534 B1 * | 2/2003 | Sawhney ............... 424/486 |
| 6,528,555 B1 * | 3/2003 | Nikutowski et al. ............... 523/116 |
| 6,593,394 B1 * | 7/2003 | Li et al. ............... 523/113 |
| 6,620,196 B1 | 9/2003 | Trieu et al. |
| 6,623,664 B2 * | 9/2003 | Takaki et al. ............... 252/511 |
| 6,648,920 B2 * | 11/2003 | Ferree ............... 623/17.11 |
| 6,528,555 B1 * | 3/2003 | Nikutowski et al. ............... 523/116 |
| 6,593,394 B1 * | 7/2003 | Li et al. ............... 523/113 |
| 6,620,196 B1 | 9/2003 | Trieu et al. |
| 6,623,664 B2 * | 9/2003 | Takaki et al. ............... 252/511 |
| 6,648,920 B2 * | 11/2003 | Ferree ............... 623/17.11 |

(Continued)

FOREIGN PATENT DOCUMENTS

EP 430517 A2 * 6/1991

(Continued)

OTHER PUBLICATIONS

Allcock, et al., *Contemporary Polymer Chemistry*, 2nd Ed., Prentice Hall, Englewood Cliffs, NJ, (1990), pp. 46-49, 582-583.

(Continued)

*Primary Examiner*—Shanon A Foley
(74) *Attorney, Agent, or Firm*—Kenyon & Kenyon LLP

(57) ABSTRACT

Provided are biocompatible viscoelastic solid materials derived from polymerization of fluid water-in-oil emulsions, along with methods of their preparation and methods for their use for tissue engineering applications, including for reforming diseased, damaged or degenerated intervertebral discs by acceptably non-invasive means.

32 Claims, 2 Drawing Sheets

U.S. PATENT DOCUMENTS

| | | | |
|---|---|---|---|
| 6,685,695 B2 | 2/2004 | Ferree | |
| 6,709,668 B2 * | 3/2004 | Won et al. | 424/426 |
| 6,716,445 B2 * | 4/2004 | Won et al. | 424/426 |
| 6,719,797 B1 | 4/2004 | Ferree et al. | |
| 6,755,863 B2 | 6/2004 | Ferree et al. | |
| D493,225 S | 7/2004 | Varga et al. | |
| 6,773,713 B2 * | 8/2004 | Bonassar et al. | 424/423 |
| 6,800,245 B1 | 10/2004 | Erbe | |
| 6,803,420 B2 | 10/2004 | Cleary et al. | |
| 6,812,211 B2 | 11/2004 | Slivka et al. | |
| 6,818,018 B1 * | 11/2004 | Sawhney | 623/11.11 |
| D501,555 S | 2/2005 | Varga et al. | |
| 6,852,127 B2 | 2/2005 | Varga et al. | |
| 6,878,384 B2 * | 4/2005 | Cruise et al. | 424/423 |
| 6,890,963 B2 | 5/2005 | Clear et al. | |
| 6,987,136 B2 * | 1/2006 | Erbe et al. | 523/114 |
| 7,025,990 B2 * | 4/2006 | Sawhney | 424/486 |
| 7,083,806 B2 * | 8/2006 | Rippon et al. | 424/484 |
| 7,097,855 B1 * | 8/2006 | Ameer et al. | 424/486 |
| 7,220,414 B2 * | 5/2007 | Brocchini et al. | 424/181.1 |
| 7,238,203 B2 | 7/2007 | Bagga et al. | |
| 7,294,617 B2 | 11/2007 | Slivka et al. | |
| 2001/0038831 A1 * | 11/2001 | Park et al. | 424/78.31 |
| 2002/0037977 A1 * | 3/2002 | Feldstein et al. | 526/60 |
| 2003/0009224 A1 | 1/2003 | Kuras | |
| 2003/0044468 A1 * | 3/2003 | Cellesi et al. | 424/487 |
| 2003/0087984 A1 * | 5/2003 | Erbe et al. | 523/113 |
| 2003/0096010 A1 * | 5/2003 | Gutowska | 424/486 |
| 2003/0170308 A1 | 9/2003 | Cleary et al. | |
| 2003/0208271 A1 | 11/2003 | Kuras | |
| 2003/0232088 A1 * | 12/2003 | Huang et al. | 424/487 |
| 2003/0235548 A1 * | 12/2003 | Lu | 424/70.12 |
| 2004/0122517 A1 | 6/2004 | Kuras | |
| 2004/0220296 A1 | 11/2004 | Lowman et al. | |
| 2005/0158358 A1 * | 7/2005 | West et al. | 424/423 |
| 2007/0005140 A1 * | 1/2007 | Kim et al. | 623/17.16 |

FOREIGN PATENT DOCUMENTS

| | | |
|---|---|---|
| WO | WO 97/26847 | 7/1997 |

OTHER PUBLICATIONS

Baldick, et al., "Bioactive Glass Increases Alkaline Phosphatase Activity In Rat Marrow Stromal Cells In Vitro," 5th World Biomaterials Conf., Toronto, II-114 Jun. 1996.

Bao, et al., "The Artificial Disc: Theory, Design and Materials," *Biomaterials* 17:1157-1167 (1996).

Costanza, et al., *Radiation Cured Coatings*, Federation of Societies for Coating Technology, Philadelphia, PA (1986), pp. 7-14.

Darwis, et al., "Characterization of PVA Hydrogel for Prosthetic Intervertebral Disc Nucleus," *Rad. Phys. & Chem.* (2001).

DeRossi, et al., "Biomimetic Macromolecular Actuators," Macro-Ion Characterization, (Smith, ed.), ACS Symposium Series 548, *Amer. Chem. Soc.*, Washington, DC, p. 518-522 (1994).

El-Ghannam, et al., "Bioactive Material Template For In Vitro Synthesis of Bone," *J. Biomed. Materials Res.* 29:359-370 (1974).

Fernstrom, "Metallic Disk Prosthesis for Lumbar," *Nord. Med.* 71:160 (1964).

Ferry, *Viscoelastic Properties of Polymers*, John Wiley & Sons, NY, p. 529-540 (1980).

Friberg, et al., "Emulsions," *Kirk Othmer Encycl. of Chem. Tech.*, 4th Ed., 9:393-413, (1994).

Hou, et al., "Lumbar Intervertebral Disc Prosthesis," *Chinese Med. J.* 104:381-386 (1991).

Iatridis, et al., "Alterations in the Mechanical Behavior of the Human Lumbar Nucleus Pulposus with Degeneration and Aging," *J. Orthopaedic Res.* 15:318-322 (1997).

Iatridis, et al., "Shear Mechanical Properties of Human Lumbar Annulus Fibrosus," *J. Orthopaedic Res.* 17:732-737 (1999).

Lanza, et al., "Polymer Scaffold Processing," *Principles of Tissue Engineering*, Second Edition eds. Academic Press, San Diego, CA, (2000).

Ray, et al., "Lumbar Interbody Threaded Prostheses," *The Artificial Disc*, (Brock et al., eds), Berlin: Springer-Verlag, pp. 53-67 (1991).

Sabolinski, "Cultured Skin As a 'Smart Material' for Healing Wounds: Experience in Venous Ulcers," *Biomaterials* 17:311-320 (1996).

Schepers et al., "Bioactive Glass Particulate Material As A Filler For Bone Lesions," *J. Oral Rehab.* 18:439-452 (1991).

Ducheyne et al., Biomaterials, 20:2287-2303 (1999).

Thomson, "Polymer Scaffold Processing," pp. 251-261 in Principles of Tissue Engineering, 2nd Ed., (Lanza et al., eds.) Academic Press, San Diego, CA, 2000.

Morrison et al., Colloidal Disperions, Wiley Interscience, NY, 2002.

Binks, Modern Aspects of Emulsion Science, Royal Society of Chemistry, Cambridge, UK, 1998.

Encyclopedia of Polymer Science and Engineering, John Wiley & Sons, New York, 1989.

* cited by examiner

POLYMERIZABLE EMULSIONS FOR TISSUE ENGINEERING

REFERENCE TO RELATED APPLICATIONS

This application is a divisional of and claims priority to U.S. patent application Ser. No. 10/977,521, filed Oct. 29, 2004, herein incorporated in its entirety, which claims priority to U.S. Provisional Patent Application No. 60/515,404, filed Oct. 29, 2003.

FIELD OF THE INVENTION

The present invention concerns compositions and methods useful for tissue engineering and bioadhesive applications, such as reforming degenerated discs of the spine of a vertebrate, particularly of a human.

BACKGROUND OF THE INVENTION

Back pain is one of the most frequently reported musculoskeletal problems in the United States, commonly caused by degeneration of a disc. The vertebrae of the spine articulate with each other to allow motion in the frontal, sagittal and transverse planes, but as the weight of the upper body increases, the vertebral bodies, which are designed to sustain mainly compressive loads, increase in size caudally. The intervertebral discs, comprising about 20-33% of the lumbar spine length, is a major link between the adjacent vertebrae of the spine, which with the surrounding ligaments and muscles, provide stability to the spine. Each disc consists of a gelatinous nucleus pulposus surrounded by a laminated, fibrous annulus fibrosus, situated between the end plates of the adjacent vertebrae. The discs sustain weight and transfer the load from one vertebral body to the next, and maintain a deformable space to accommodate normal spine movement.

The nucleus pulposus contains collagen fibrils and water-binding glycosaminoglycans, while the surrounding annulus fibrosus comprises fibrocartilaginous tissue and fibrous protein arranged in 10 to 20 lamellae forming concentric rings around the nucleus pulposus. The collagen fibers within each lamella are parallel to each other, angled at ~60° from vertical, and alternating in direction of the inclination for each lamellae. This crisscross arrangement enables the annulus fibrosus to withstand torsional and bending loads. The endplates comprise hyaline cartilage, and are directly connected to the lamellae, forming the inner one-third of the annulus.

Under compressive loads, the nucleus pulposus flattens and bulges radially outward; while the annulus fibrosus stretches, resisting the stress. The end-plates of the vertebral body also resist the ability of the nucleus pulposus to deform. Thus, pressure is applied against the annulus and the endplate, transmitting the compressive loads to the vertebral body. Conversely, when tensile forces are applied, the disc is raised, straining the collagen fibers in the annulus. When the individual bends, one side of the disc is in tension while the other side is in compression, and the annulus on the compressed side bulges outward.

When the disc is subjected to torsion, shear stresses are applied. As an individual ages, repeated rotational loading initiates circumferential tears in the annulus fibrosus, which gradually causes radial tears in the nucleus pulposus, resulting in degradation and water loss at the rupture. Consequently, over time a disc looses its ability to resist compressive loads as the annulus bulges. As the severity of the tear increases, much of the disc contents are lost, leaving only a thin line of fibrous tissue at the nuceous pulposus—a condition known as disc resorption. As the annulus bulges posteriorly into the spinal canal, compression of the nerve root results in sciatica. Once the disc ruptures, excessive motions can cause in spine segmental instability, making the spine more vulnerable to trauma and degenerative spondylolisthesis and increasing pain.

Surgical treatments for herniated disc include laminectomy, spinal fusion and disc replacement with prostheses. However, the results of spinal fusions are varied, even with autografts, and result in total elimination of motion at the fused joint and often significant long-term limitations. Therefore, as an alternative to spinal fusion, intervertebral disc prostheses have been used to replace and simulate the function of a normal disc. Disc replacement prostheses must be biocompatible and capable of sustaining weight and transferring load from one vertebral body to the next. Such a prosthesis should last for the lifetime of the patient and have sufficient mechanical strength to resist injury during movement, while maintaining a deformable space between the vertebrae to accommodate movement. More importantly, the replacement disc should be able to be fixed to the adjacent vertebrae, but should not cause damage if the disc fails.

Many artificial disc designs have been used or proposed. Devices for total disc replacement have ranged from metal ball bearings with a silicone rubber nucleus and silicone fluid-filled plastic tube, to spring systems, elastic disc prosthesis, and elastic discs encased in a rigid column. Unfortunately, over time such devices have proven to offer inadequate mechanical performance and unlikely long-term bone fixation.

However, replacing only the nucleus prosthesis has several important advantages over total disc replacement. The nucleus has a much simpler structure and function than the annulus and endplates, so that with proper design of the nucleus prosthesis the surgeon can leave the annulus and endplates intact. Only the spatial and mechanical properties of the annulus are replaced to relieve the compressive load on the disc. This permits the remaining disc tissues and their functions to be retained, while requiring only a minimally invasive surgical procedure, such as endoscopic implantation through a small incision in the annulus. The implant can be designed so that no fixation to the vertebra is required.

Various attempts have been made to develop prostheses for the nucleus, using for example, metal (Fernstrom, *Nord. Med.* 71:160 (1964)), or various elastomers (either preformed or formed in situ) (Hou et al., *Chinese Med. J.* 104:381-386 (1991), but proved to lack biocompatibility and mechanical strength. Bao et al. designed a much more effective artificial intervertebral disc nucleus (Bao et al., *Biomaterials* 17:1157-1167 (1996); U.S. Pat. Nos. 5,047,055 and 5,192,326) using hydrogel materials containing approximately 70% water content under physiological loading conditions. The hydrogel nucleus implant mimics the capacity of the nucleus tissue to absorb and release water under cyclic loading conditions, thereby mechanically restoring disc anatomy and function, without adverse local or systemic tissue reaction. Hydrogels have several major mechanical drawbacks. By definition, they operate by absorbing water after cross linking, but for example, in the degenerated disc site, water absorption cannot be controlled. Moreover, water absorption is a reversible process, i.e., the water is also lost from a hydrogel implant, as well as absorbed—which again renders control of hydration very difficult. In addition, the thermal activation procedures necessary to achieve crosslinking of some of the hydrogels are notoriously difficult to control.

An interbody rigid, threaded nucleus implant has been clinically used, see Ray et al., *The Artificial Disc*, (Brock et al., eds), Berlin: Springer-Verlag, 1991, pp 53-67; U.S. Pat. Nos. 4,772,287, 4,904,260 and 5,674,295. The prostheses have a hydrogel core constrained by a flexible, but inelastic woven polyethylene-fiber jacket intermingled with bioresorbable materials to attract tissue ingrowth, but implantation requires discectomy using a larger-than normal incision. However, the prosthesis materials are purely synthetic, including no cells or developing tissue. More recently, to minimize implant extrusion and minimize invasive surgery Advanced BioSurfaces has developed a system featuring a polymer formulation delivered through a balloon catheter using a polymer-injection gun (U.S. Pat. No. 5,888,220). Polyurethane is used and cured in situ to provide strong mechanical properties. However, many of the components of the system lack biocompatibility, and the use of a balloon catheter leads to a more involved treatment procedure and mechanical limitations upon treatment.

For repairing skin tissue, particularly of burn patients or for decubitus wounds, cells have been seeded onto templates of either resorbable or non-resorbable material and dressed onto the wound site (Sabolinski, *Biomaterials* 17:311-320 (1996)). However, tissue engineering of the skin is significantly different from tissue engineering of the intervertebral disc, requiring completely different tissue compositions and unique mechanical requirements.

U.S. Pat. Nos. 5,108,438 and 5,258,043 teach a porous matrix of biocompatible and bioresorbable fibers which may be interspersed with glycosaminoglycan molecules to form a scaffold matrix for regenerating disc tissue and replace both the annulus fibrosus and nucleus pulposus. However, replacement of so much tissue is a relatively invasive procedure, requiring lengthy recovery time. Furthermore, these matrices include no cells to stimulate tissue recovery, nor is there any incipient tissue formation in this device at the time of implantation. Polymeric scaffolds for tissue engineering are well known (e.g., Thomson, "Polymer Scaffold Processing," pp. 251-261 in *Principles of Tissue Engineering*, $2^{nd}$ Ed., (Lanza et al., eds.) Academic Press, San Diego, Calif., 2000). However, use of these pre-made structures require extensive surgery.

Various bioactive glass materials (e.g., U.S. Pat. No. 5,204, 104) have been seeded with cells in order to facilitate cell function including proliferation and extracellular matrix synthesis, e.g., El-Ghannam, et al., *J. Biomed. Materials Res.* 29:359-370 (1974), Schepers et al., *J. Oral Rehab.* 18:439-452 (1991) and U.S. Pat. No. 5,204,106, have been used. In addition, dense bioactive glass discs have been found to enhance osteoprogenitor cell differentiation (Baldick et al., Transactions 5th World Biomaterials Conf., Toronto, II-114 (June 1996), and have been seeded with cells in order to facilitate cell function including proliferation and extracellular matrix synthesis, e.g., El-Ghannam, et al., *J. Biomed. Materials Res.* 29:359-370 (1974), Schepers et al., *J. Oral Rehab.* 18:439-452 (1991) and U.S. Pat. No. 5,204,106.

U.S. Pat. No. 5,964,807 teaches a method for evacuating degenerated nucleus pulposus tissue from the intervertebral disc, then implanting into the evacuated nucleus pulposus space, a hybrid material prepared by combining intervertebral disc cells with a biodegradable substrate comprising bioactive glass, polymer foam, or polymer foam coated with sol gel bioactive material. The polymer foam comprises copolymers of D,L poly(lactide-co-glycolide). The process includes isolating viable cells from the nucleus pulposus of an intervertebral disc and culturing the cells on the biodegradable substrate prior to implantation, or culturing the cells prior to combining them with the biodegradable substrate immediately prior to implantation. But the resulting implant lacks the required viscoelastic properties of the healthy nucleus pulposus, e.g., Iatridis et al., *J. Orthopaedic Res.* 17:732-737 (1999); Iatridis et al., *J. Orthopaedic Res.* 15:318-322 (1997).

Liquid and foam emulsions have been described for the preparation of polymeric scaffolds for tissue engineering; e.g., U.S. Pat. Nos. 6,337,198 and 6,103,255 teach the preparation of porous polymer scaffolds from an emulsion of a selected polymer and multiple solvents, then driving off the solvents to form pores, thereby creating a scaffold. These approaches require that first the polymer is formed, and then it is emulsified. However, polymerization of the scaffold is thermal-based, making polymerization in situ in the patient unacceptable there may be residual organic solvents that could cause inflammatory or toxic reactions.

Water-in-oil (inverse) ("W/O") emulsions consisting of a discrete aqueous phase and an organic, typically hydrocarbon, continuous phase have diverse uses in coatings, adhesives, water treatment, cosmetics, personal care and pharmaceuticals. W/O emulsions are valuable largely because they supply high concentrations of water-soluble "active agents" in a liquid, free-flowing form. See, e.g., Friberg, et al., "Emulsions," in *Kirk Othlner Encyclopedia of Chemical Technology*, $4^{th}$ Ed., Vol. 9, pp.393-413, 1994. Such active agents may include one or more components, e.g., high molecular weight, water soluble polymers for water treatment, or organic salts, e.g., many drugs for treatment of disease.

Processes for the polymerization of reactable monomers and oligomers are well know in the art, and are commonly used industrially for preparing coatings, inks, and other polymeric systems. See, e.g., generally, Allcock et al., *Contemporary Polymer Chemistry*, $2^{nd}$ Ed., Prentice Hall, Englewood Cliffs, N.J., 1990, p. 553. Often light, particularly UV light, is used to initiate the polymerization process, e.g., photopolymerization.

EP 0430 517(A2) teaches biomosaic polymers formed from W/O emulsions and microemulsions, used to produce membranes for assays, separations, and catalysis processes that require the binding of biologically active materials, e.g., proteins, enzymes, DNA, antigens and antibodies, at the polymerized surfaces. The exemplified monomers are isobornyl acrylate and methyl methacrylate, and binding of the active materials may be chemical or physical, depending on the intended use. The methods taught include photoinitiated polymerization of the surfactant-stabilized emulsions. Similarly, U.S. Pat. No. 5,151, 217 discloses bicontinuous microemulsions in which both the organic (oil) phase and the aqueous (water) phase contain polymerizable organic monomers. The aqueous phase also contains a polymerizable surfactant, and apparently polymerization may be activated by the inclusion of photoinitiators. Conversely, oil-in-water ("O/W") emulsions, wherein water is the continuous phase, representing a structural mechanical component of the final product, polymerization has also been photoinitiated, e.g., generally, Costanza et al., *Radiation Cured Coatings*, Federation of Societies for Coating Technology, Philadelphia, Pa., 1986; U.S. Pat. No. 6,045,972.

Polymers also can be prepared in gel form. The polymer gel is essentially a crosslinked solution, linked by chemical bonds, crystallization or other kinds of junctions made by means of the chemical properties of the monomers within the polymer. "Hydrogels" are a specific class of polymer gels, comprising crosslinked polymer networks of hydrophilic, water soluble or water dispersible polymers, including polyelectrolytes, which are permeated by, and swell in, aqueous media—but do not dissolve therein (Ferry, *Viscoelastic Properties of Polymers*, John Wiley, NY, 1980, p.529; Allcock et al., supra; DeRossi et al., in *Macro-Ion Characterization*, (Smith, ed.), ACS Symposium Series 548, Amer. Chem. Soc., Washington, D.C., 1994, p. 20).

Injectable hydrogels, gelatins and similar polymeric carriers for tissue engineering applications are well known in the art. For example, in U.S. Pat. No. 6,224,893, Langer et al. teach the use of interpenetrating polymer networks that form hydrogels for drug delivery and tissue engineering, reportedly useful for injectable, photocurable cell scaffold formation. However, these interpenetrating networks and the precursor components comprise single-phase dispersion requiring two or more polymers, the crosslinking of which results in a continuous hydrogel state with limited mechanical properties.

Ideally, intervertebral disc treatment would guide and stimulate reformation of damaged or diseased intervertebral disc tissue, especially nucleus pulposus and annulus fibrosus tissue. Currently, however, although hydrogel and tissue engineering models have been tried, there is still not a good therapeutic approach for reconstructing damaged discs, using non-toxic, biocompatible replacement materials that will not elicit an autoimmune or inflammatory response that might result in rejection. Such materials should be deliverable in a fluid or gel state by minimally invasive methods, but which when set, should fill the entire internal space of the intervertebral disc to provide mechanical properties comparable to the nucleus pulposus. Thus, a need for such a material has remained until the present invention.

SUMMARY OF THE INVENTION

The present invention meets the foregoing needs by providing an effective, therapeutic approach for reconstructing damaged discs, using a non-toxic, biocompatible inverse emulsion (water-in-oil) that does not provoke an autoimmune or inflammatory response. Yet the emulsion can be delivered to the body by minimally invasive means, and conform to the complex shapes of the tissue structures requiring repair or reconstruction. After polymerization in situ and/or in vivo, the resulting gel retains a controlled viscoelasticity matching the mechanical requirements of tissues or organs, such as the nucleus pulposus of the intervertebral discs. The resulting biocompatible tissue engineering products of the present invention comprise the polymerized matrix resulting from the emulsion alone, as well as the emulsion with the addition of glass or bioactive glass components, viable cells, enhancers, stabilizers, photoreactors, and the like, that improve the performance, stability and durability of the product for use in vivo, particularly for reforming degenerated, damaged or diseased intervertebral discs.

It is an object of the present invention is to provide a biocompatible, non toxic, inverse (water-in-oil) fluid emulsion for tissue engineering, comprising two discrete organic and aqueous phases, wherein the organic phase comprises one or more reactive, ethylenically unsaturated monomers, oligomers or mixtures thereof, which when said emulsion is polymerized in situ, forms a strong, cohesive viscoelastic material comprising two discrete organic and aqueous phases.

It is another object of the present invention to provide a method of preparing a strong, biocompatible viscoelastic material for tissue engineering, having two discrete organic and aqueous phases, said method comprising preparing a biocompatible, non toxic, inverse (water-in-oil) fluid emulsion comprising two discrete phases (organic and aqueous), wherein the organic phase comprises one or more reactive, ethylenically unsaturated monomers, oligomers or mixtures thereof; and polymerizing said emulsion in situ.

It is yet another object to provide a strong, biocompatible viscoelastic material for tissue engineering, wherein the material has two discrete phases (organic and aqueous).

Still another object is to provide methods for using the biocompatible viscoelastic material, wherein the methods comprise forming the emulsion into tissue implants, scaffolds for cell growth, or bioadhesives for joining or repairing living tissue. The emulsion is delivered to the site in need of repair, regeneration or tissue engineering in a mammal, and polymerized in situ into a biocompatible viscoelastic material in situ, preferably delivery is accomplished by acceptably non-invasive means, such as by injection. In particular, the provided methods teach replacing or repairing at least one intervertebral disc in the spinal column of the mammal, and comprising delivering the emulsion into an evacuated region of the nucleus pulposus of the intervertebral disc of the mammal and then polymerizing the emulsion in situ to form the viscoelastic material, thereby forming an implant in the mammal. The method may further include fully or partially evacuating a degenerated nucleus pulposus from the intervertebral disc of the mammal by minimally invasive surgical means, prior to delivering the emulsion.

The advantages of the present invention over prior art include good spatial and temporal control, fast-curing at room temperature or physiological temperatures, and minimal heat production during polymerization. The emulsions have the ability to form complex shapes that conform to the tissue structures targeted for repair or reconstruction, yet after polymerization the gel-like product retains controlled viscoelasticity matching the mechanical requirements of the tissues or organs, such as the nucleus pulposus of the intervertebral discs. Moreover, the porous aqueous environment of the novel emulsions facilitates cell regeneration, and permits the addition of active agents that enhance, stabilize and modulate the effectiveness of the resulting biocompatible tissue engineering products and the methods of use thereof.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended drawings. It should be understood, however, that the invention is not limited to the precise arrangements and instrumentalities shown.

DETAILED DESCRIPTION OF CERTAIN EMBODIMENTS OF THE INVENTION

Figure 1:
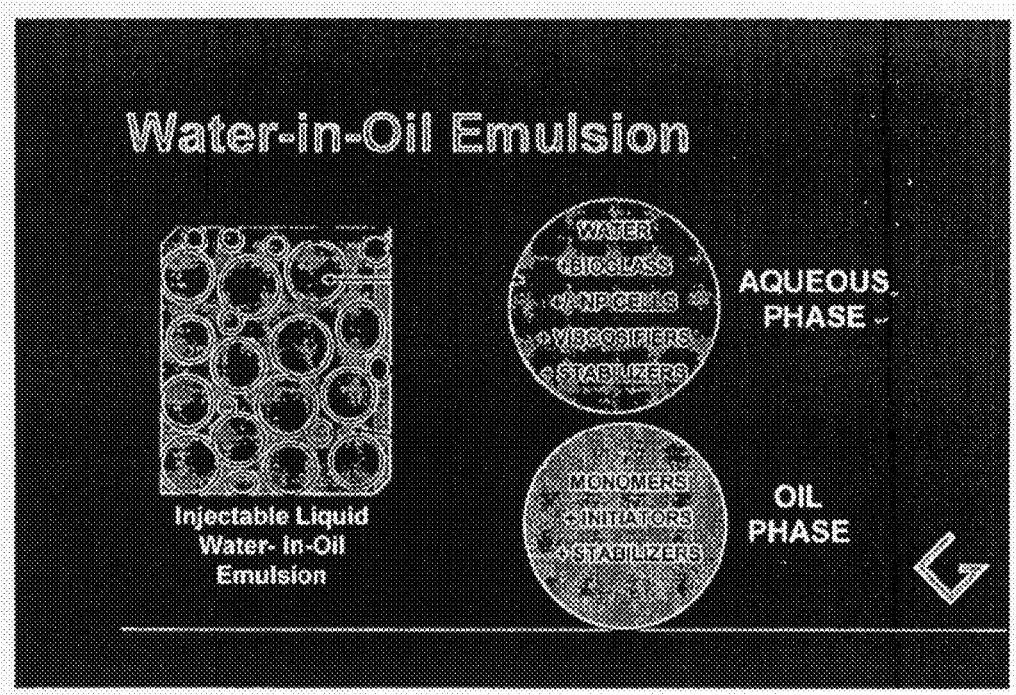
FIG. 1 illustrates the basic composition of a fluid water-in-oil emulsion.
Figure 2:
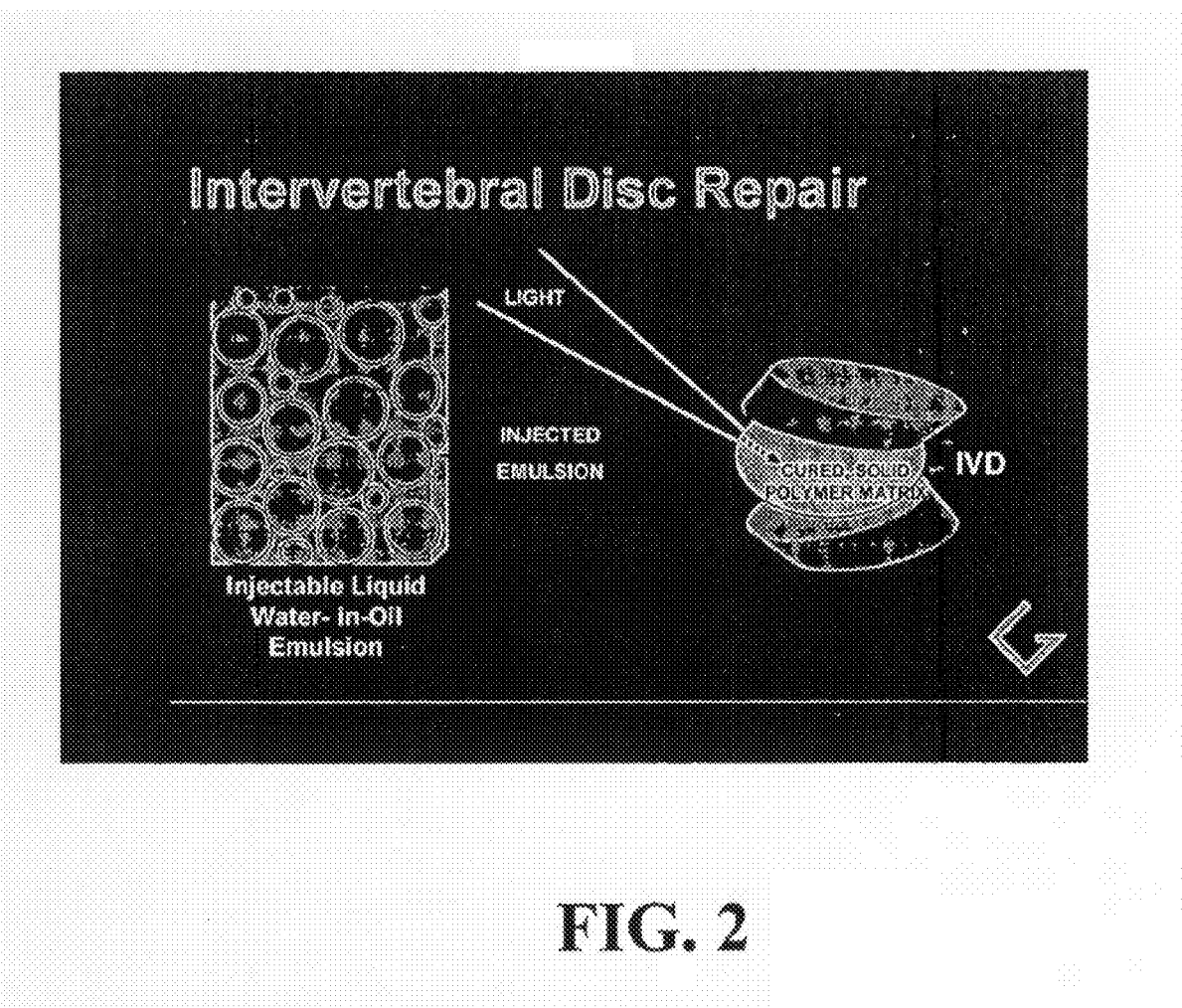
FIG. 2 illustrates and exemplifies an embodied method of injecting the emulsion shown in FIG. 1, and photoactivating polymerization and curing to produce a matrix for use in tissue engineering, specifically for reconstructing an intervertebral disc.

The present invention provides a fluid, water-in-oil ("W/O") emulsion of the form presented in FIG. 1, that is polymerizable in situ and/or in vivo into a viscoelastic, soft, flexible and cohesive gel matrix that is particularly useful for tissue engineering and bioadhesive applications, including reconstructive surgery, such as in the repair of the nucleus pulposus of intervertebral discs. The emulsions used for the tissue engineering scaffolds are necessarily biocompatible, non-toxic and easily processed into complex shapes, while the resulting polymerized gels possess the physical characteristics necessary to allow for large surface to volume ratios and the mechanical strength needed for bone or tissue substitutes. While flexible, the resulting polymeric gel matrix is rigid enough to maintain the desired shape under in vivo conditions.

The polymers in this invention are expressly not biodegradable, and as a result the system survives for many years in vivo, thereby reducing or eliminating the need for additional procedures. The porous structure of the polymerized matrix in certain preferred embodiments also acts as an adhesive substrate enhancing cellular ingrowth, while allowing retention of differentiated cell function. Bioactive glasses and additional active agents may also be present. The basic composition of the W/O emulsion is illustrated in FIG. 1.

The present invention demonstrates that inverse W/O emulsions can be formed having an organic phase and an aqueous phase. Surprisingly, when the organic phase, containing one or more reactable, polymerizable organic monomers and/or oligomers, as an essential component, is combined with an aqueous phase comprising water, polymer solutions and dispersions, salts, pigments, and other active agents, solution and dispersion components, such as inorganic, organic and ceramic biological cell growth stimulators, as well as optionally, viable cells and the like, the resulting emulsions are both novel and useful. Water is always present in some amount in the aqueous phase. The selection of the reactable monomers and polymers chosen for the emulsions of the present invention enable the viscoelasticity and porosity of the polymerized gel products to be adjusted to meet the requirements of the various intended applications. The organic phase may also optionally contain high molecular weight polymer and polymerization initiators, such as photoinitiators in a preferred embodiment, or the reactive organic monomers and/or oligomers may contain biocompatible, low toxicity, long chain fatty acid moieties such as are found in natural fats and biological cell membranes, including butyric, caproic, caprylic, capric, lauric, myristic, palmitic, palmitoleic, stearic, oleic, linoleic, linolenic, ricinoleic, gadoleic, arachidonic, behenic, cetoleic and erucie. Accordingly, the present emulsions comprise a wide range of useful compositions and ratios that have been unknown in the prior art for tissue engineering purposes.

In the present invention, "fluid" refers to a form of matter, in this case an emulsion, that cannot permanently resist any shearing force that causes flow, although technically the liquid can be one continuous phase, whereas the present emulsion is differentiated from such a liquid in that the "emulsion" comprises at least two immiscible components held together by chemical forces. "Viscosity" refers to internal fluid friction or the extent to which a fluid resists flow under an applied force, measured as the ratio of shear stress to the rate of shear of a fluid. A "polymer gel" is any polymeric material in which there are physical or chemical associations between the individual polymer chains that cause them to have restricted motion and typically to have a 3-dimensional structure than may enable solvent ingress and swelling. The polymer gels of this invention are solid materials that deform "viscoelastically," providing a flexibility or pliability in response to applied external stress.

The emulsions and the resultant polymerized polymeric systems of the present invention represent distinct and uniquely useful 2-phase compositions, having discrete hydrophilic and hydrophobic phases, both in the emulsion before polymerization and in the gel after polymerization. Therefore, a W/O emulsion of the present invention, as depicted in FIG. 1, by definition, is not a hydrogel. Hydrogels are defined in the Grant & Hackh's Chemical Dictionary, as a water-swollen, rigid, three-dimensional network of cross-linked, hydrophilic macromolecules (20-95% water). Accordingly, hydrogels constitute a completely different class of compounds from W/O emulsions used in the present invention, and the present W/O compositions represent a marked improvement over the hydrogel technology, particularly for nucleus pulposus reconstruction and replacement. The mechanical and elastic properties of the present technology do not depend on any reaction in situ, such as water absorption in situ, and it require no thermal energy to effect crosslinking needed in a hydrogel.

The previously discussed Buttery application, EP 0430 517 A2, therefore, differs from the present invention in that it utilizes a hydrogel. By comparison, the present invention recognizes that only certain biocompatible monomers may be useful, and that the aqueous phase droplet size must be of sufficient size to permit the inclusion of glasses, viable biological cells, bioactive glass or other components in a form and amount sufficient to permit these critical aqueous phase components to diffuse into surrounding regions as required for biological tissue formation. Further, the present invention is directed to in vivo polymerization of the water-in-oil emulsion, rather than in vitro preparation of biological assay membrane materials disclosed by Buttery.

The hydrophobic, organic phase of the preferred emulsions of the present invention, comprises any well-known monomer, i.e., ethylenically unsaturated monomers. Acrylates are the typical, general and preferred class of monomers used in the present invention, including in certain preferred embodiments of the present invention, without intended limitation, are: methyl acrylate; methyl methacrylate; ethyl acrylate; ethyl methacrylate; stearyl acrylate and methacrylate; lauryl acrylate and methacrylate; ethoxylated and/or propoxylated acrylates and methacrylates; alkoxylated acrylates and methacrylates; allyl acrylates and methacrylates; tetrahdrofurfuryl methacrylate; isodecyl acrylate or methacrylate; octyldecyl acrylate and methacrylate; phenoxyethyl acrylate and methacrylate; glycidyl acrylate and methacrylate; isobornyl acrylate; caprolactone acrylate; ethoxylated nonyl phenol acrylates and methacrylates; propylene glycol acrylate and methacrylate; alkoxylated nonyl phenol acrylates and methacrylates; alkoxylated diol diacrylates; alkoxylated bisphenol diacrylates; ethylene glycol diacrylate; butylene glycoldiacrylate and dimethacrylate; butanediol diacrylate and dimethacrylate; neopentylglycol diacrylate and dimethacrylate; polyethyleneglycol diacrylate and dimethacrylate; ethoxylated bisphenol diacrylates; saturated and unsaturated (C36) dimer diol diacrylates; polyethyleneglycol diacrylate and dimethacrylate; polybutadiene diacrylate and dimethacrylate; polybuadiene urethane diacrylate; triethylene glycol dimethacrylate; acrylamide and methacrylamide; homopolymers of the monomers, as well as copolymerization of mixtures of monomers. Those skilled in the art will be familiar with other monomers that can be used to prepare polymers, and which are useful in the organic phase of the present invention. Pre-polymerized lauryl acrylate can be used as a thickening agent to replace part of the monomer in the oil phase.

In many instances involving W/O emulsions, the hydrocarbon phase has no role in the actual performance of the active product that is generally contained in the aqueous phase. In some cases, organic hydrocarbon phase components can even represent an unwanted problem which adversely affects certain properties either directly related to the performance of the actives or because of environmental concerns. This is particularly true for applications, such as industrial coatings, water treatment or papermaking, and for biomedical applications such as tissue engineering, wherein organic solvents can cause inflammatory and toxic responses in the patient. Conversely, in certain applications, such as in tissue engineering, after polymerization, the resulting viscoelastic organic polymer phase becomes an integral and functional part of the system. In the present situation, polymerization of the reactable monomers alleviates any potential problem associated with unwanted organic phase components.

The actual steps necessary to generate an emulsions are well known in the art, e.g., as generally discussed by Morrison et al., *Colloidal Dispersions*, Wiley Interscience, NY, 2002; and Binks, *Modern Aspects of Emulsion Science*, Royal Society of Chemistry, Cambridge, UK, 1998. For example, the water-in-oil emulsion can be achieved by subjecting the mixture to high shear mechanical agitation with the RPM ranging from 1500 to 4000; Alternatively, or in combination with high shear mechanical agitation, the mixture may be subjected to high pressure homogenization using commercially available high pressure homogenizers. When homogenization is employed it can be single stage or dual stage with applied pressures ranging from 150 to 1500 bars.

Water and oil emulsions generally contain quantities of hydrocarbons or other hydrophobic organic components, and water or aqueous solutions (typically 10% to 80% of each, respectively), together with one or more surfactants contained in one or both phases to stabilize the emulsion. In some systems, the surfactant(s) are selected for the primary purpose of enabling inversion of the emulsion from W/O (water-in-oil) to O/W (oil-in-water), as may be required for particular industrial applications and may include, without limitation, one or more linear or branched alkanes or alkenes with one or more hydroxyl, carboxyl, amine including quaternary amine, alkoxyl, or saccharide groups, or mixtures of these, or salts of these, including lithium, sodium, potassium, calcium, magnesium and zinc salts of stearates, oleates, and other fatty acids; polymers of propylene glycol or copolymers of propylene glycol and ethylene glycol; a siloxane or alkyl siloxane surfactant compound; a fluorinated surfactant compound; or mixtures of these.

The temperature of the system often determines the stability and form of the emulsion (i.e., whether the emulsion is W/O or O/W). W/O is the preferred, and actually the required form of emulsion for this invention. The temperature ranges for the production of a W/O emulsion is strong function of composition of the component phases. For example, temperatures are very low for ice cream or butter, and range to very high for petroleum in secondary oil recovery. The stability of the emulsion further depends on a variety of additional factors including, but not limited to, the method of preparation, the size of the droplets in the dispersed phase, the concentrations and types of surfactants and salts that are present, and other factors.

Accordingly, the organic phase of the preferred embodiments may be polymerized by any means, such as by thermal initiation, or other well-known reaction processes. But in a preferred embodiment polymerization is initiated by photo-initiation means, such by the use of electromagnetic radiation, including ultraviolet, visible, infrared light and microwaves, such that the resultant polymerized organic components form an in-situ, preferably in vivo, solid phase surrounding the dispersed aqueous phase. The pore structure is a function of the amount of aqueous phase present, the amount and type of surfactant used to stabilize the dispersed aqueous phase and the amount of energy used to disperse the aqueous phase into droplets in the emulsion. In this case, upon curing, the pores are not hollow pores, as in many tissue scaffolds; rather, the dispersed stable water droplets range in size from nanometers to microns. Such systems provide a porous matrix capable of delivering active components to a targeted substrate. These substrates can include those of industrial importance, for example, metallic or other coated surfaces, and those of biomedical importance, for example, tissue engineering applications such as for intervertebral discs, cartilage and bone.

In tissue engineering, polymeric matrices are known to support cell growth and provide a means for insertion or application of the active cells or cell growth stimulators to a target organ or tissue. The viscoelastic properties of the present polymers are critical to certain of these applications, such as in the repair of the nucleus pulposus of intervertebral discs. The reactable monomers and polymers chosen for the emulsions of this invention enable the viscoelasticity and porosity of the reacted gel products to be adjusted to meet the requirements of various applications.

The aqueous phase of the preferred embodiments can contain any water-soluble or water-dispersible polymer, which can be prepared in a substantial concentration in water. Thus, the concentration of the aqueous phase in the emulsion of the present invention can range from about 0.5% to about 90% weight/weight of the hydrophobic oil phase consisting of monomers and the like, more preferably from about 5.0 wt % to about 75 wt %, still more preferably from about 10 wt % to about 50 wt %, most preferably from about 0.5 wt % to 15 weight percent, and from 15 wt % to about 30 wt %. Stabilizers and stabilizing salts, as will be identified below and the like, can be beneficially added to the aqueous phase.

As a result, the present invention is readily distinguished from U.S. Pat. No. 5,151,217 (Price), in that the aqueous phase of the present emulsion is not polymerizable, and the microemulsions of the '217 patent, by definition, have aqueous particle sizes in the nanometer range—too small to accommodate viable biological cells and active materials.

The W/O emulsions contemplated by the invention can be made with, or without, the addition of high molecular weight polymers in the organic phase, hence, the initial viscosity of the emulsion is variable, which enables great flexibility of use. However, additional polymers may be added to the aqueous phase, usually prepared by free radical initiation; and condensation polymers, usually prepared without special initiators. Polymers of this type are known in the art, and may be of synthetic or natural origin. Those of synthetic origin may include polyelectrolytes, such as polyacrylic acid, polystyrene sulfonate, polyethylene oxide, polypropylene oxide, copolymers of ethylene oxide and propylene oxide, and other synthetic polymers well-known in the art. Those of natural origin may include polysaccharides, proteins, proteoglycans, nucleic acids and other natural polymers well-known in the art, including those which may be synthetically-modified, such as hydroxyethylcellulose and carboxymethylcellulose. Those skilled in the art recognize that for many of the applications for which these polymers are useful, activity of the polymers will increase as the molecular weights increase.

Essentially any non-toxic biocompatible substance that is readily soluble in the aqueous phase of the emulsion may be added. Descriptions of polymers suitable for addition to the aqueous phase may be found, for example, in *Encyclopedia of Polymer Science and Engineering*, John Wiley & Sons, New York, 1989; pharmaceutically-acceptable compositions are also described, for example, in *Remington's* Pharmaceutical Science, Mac Publishing Co., (Gennaro, ed.), 1985. materials are non-toxic to a patient at the dosages and concentrations employed, and include without limitation, diluents; solubilizers; lubricants; suspending agents; encapsulating materials; solvents; thickeners; dispersants; buffers, such as phosphate, citrate, acetate and other organic acid salts; anti-oxidants, such as ascorbic acid; preservatives; low molecular weight peptides (less than about 10 residues), such as polyarginine; proteins, such as serum albumin, gelatin or immunoglobulins; hydrophilic polymers, such as poly(vinylpyrrolin-dinone); amino acids, such as glycine, glutamic acid, aspartic acid or arginine; monosaccharides; disaccharides and other carbohydrates, including cellulose or its derivatives; glucose; mannose; dextrines; chelating agents, such as EDTA; sugar alcohols, such as mannitol or sorbitol; counter-ions, such as sodium and/or non-ionic surfactants ,such as Tween, pluronics or PEG. Stabilizers and stabilizing inorganic salts may include, e.g., hyaluronic acid, sodium hyaluronate, hydroxypropyl methyl cellulose, sodium chloride, alkali metal and alkaline earth metal halides, potassium chloride, calcium carbonate, sulfates, such as calcium sulfate, phosphates, magnesium chloride, and the like.

Embodiments also encompass the use of pharmaceutically acceptable carriers to deliver pharmaceutical additives to the aqueous phase of the polymerizable emulsion. Exemplary pharmaceutically acceptable carriers include, but are not limited to, water, saline, starch, hydrogel, polyvinylpyrrolidone, polysaccharide, hyaluronic acid ester, and plasma, with water being preferred. Buffering agents, if present, are typically present in the activated form, in a concentration of from about 0-0.1 mg per 100 ml of the pharmaceutically acceptable carrier, or from about 0.08 mg to about 0.1 mg per 100 ml of the pharmaceutically acceptable carrier. The lyophilized powder form for the injectable may typically comprise from 0-0.2% by weight, or from about 0.09% to about 0.11% by weight buffering agent, if any.

These emulsions may further contain particulate organic/inorganic fillers, such as radio-opacifiers, polymeric microspheres, glass or bioactive/bioinert glass (silanized and/or non silanized), from 0.5% to 70% wt/wt of the emulsion. Because bioactive glass is inherently more reactive than inert glasses, the quantity of bioactive glass that can be added, is in part limited to an amount that does not interfere with the polymerization of the emulsion. Crystals of sugars may also be used, as well as microspheres of water-soluble polymers, or proteins, such as albumin. Accordingly, the aqueous phase droplet size of the present invention must be of sufficient size ($\geq 1$ micron) to allow for inclusion of viable biological cells, glasses, bioactive glass or other components.

An emulsifier, such as sorbitan monooleate and the like, is added to the emulsion in the range of 0.1% to about 5.0% by weight of the emulsion.

The preferred polymerized viscoelastic material comprises biocompatible and non-toxic materials having chemical structures consistent with biological molecules present in cell membranes, and mechanical properties comparable to the nucleus pulposus or other biological tissues that may be targeted for repair or regeneration. Consequently, the present invention also encompasses injectable implants that comprise a medicament. Such medicament may include any bioactive composition, pharmaceutical, drug or compound which one desires to administer to the site of the implant. Additives may be provided in physiologically-acceptable carriers, excipients, stabilizers, and the like, and may be provided in sustained release or timed release formulations. The additives may also incorporate agents to facilitate their delivery, such as antibodies, antibody fragments, growth factors, hormones, or other targeting moieties, to which the additives are coupled. This approach provides an alternative to a nucleus prosthesis or bioadhesive that consisting solely of the polymerized materials.

For example, the medicament may comprise an anesthetic to decrease the pain or discomfort associated with injecting the implant or a composition that facilitates the integration of the polymer or decreases the trauma to the injection site. Exemplary anesthetics include, but are not limited to, lidocaine, xylocaine, novocaine, benzocaine, prilocaine, ripivacaine and propofol. Typically the anesthetic will be used with an aqueous base, and thus will be mixed with the pharmaceutically acceptable carrier and added to the injectable emulsion prior to administration.

Other medicaments that can be employed in the injectable emulsions disclosed herein include one or more of the following: tissue regeneration agents, antibiotics, steroids, fibronectins, cytokines, growth factors, analgesics, antiseptics, alpha-, beta, or gamma-interferon, erythropoietin, glucagons, calcitonin, heparin, interleukin-1, interleukin-2, filgrastim, cDNA, DNA, proteins, peptides, HGH, luteinizing hormone, atrial natriuretic factor, Factor VIII, Factor IX, and follicle-stimulating hormone. Additional pharmaceutical compounds that may be useful in the present invention include, without intended limitation, acyclovir, cephradine, malfalen, procaine, ephedrine, adriomycin, daunomycin, plumbagin, atropine, quanine, digoxin, quinidine, biologically active peptides, cephalothin, proline and proline analogues, such as cis-hydroxy-L-proline, penicillin V, aspirin, ibuprofen, steroids, nicotinic acid, chemodeoxycholic acid, chlorambucil, and the like, as well as, cell attachment mediators, such as the peptide containing variations of the "RGD" integrin binding sequence known to affect cellular attachment, and biologically active ligands. Particularly useful additions include substances that enhance or exclude particular varieties of cellular or tissue in-growth, for example, but again without limitation, osteoinductive substances, such as bone morphogenic proteins (BMP), epidermal growth factor (EGF), fibroblast growth factor (FGF), platelet-derived growth factor (PDGF), insulin-like growth factor (IGF-I and II), TGF-beta, and the like.

In an alternative embodiment, the invention permits the inclusion of bioactive glass to stimulate cellular in-growth and enhance cell growth in general, and also permits the inclusion of viable biological cells, such that healthy new tissue can be regenerated. In particular, the aqueous phase of the emulsion may contain biological cells of human or other origin.

Dissociated cells, such as chondrocytes or hepatocytes, have been used in matrixes to artificially create a three-dimensional tissue or organ, and would be suitable for use in the present invention. However, any type of cell can be added to the present emulsions for implanting into a patient, including without intended limitation, cells of the muscular and skeletal systems, such as chondrocytes, fibroblasts, muscle cells and osteocytes, parenchymal cells such as hepatocytes, pancreatic cells (including Islet cells), cells of intestinal origin, and other cells such as nerve cells and skin cells, either as obtained from donors, from established cell culture lines, or even before or after genetic engineering. These may be individual cells or tissue fragments derived from in vivo or in vitro tissue culture processes, by any of the methods described in this invention, such as photopolymerization. Consequently, a number of different cell types can be implanted into the patient in the same structure.

The cells are obtained from a suitable donor, or autologously from patient into which they are to be implanted. Cells are dissociated using standard techniques and seeded into the emulsion. Optionally, in vitro culturing may be performed to expand the cells prior to implantation. Alternatively, the emulsion is injected, polymerized and cured, and then allowed to vascularize, after which additional cells may be injected into the polymerized product. Methods and reagents for culturing cells in vitro and implantation of a tissue scaffold are known to those skilled in the art.

Glasses in the polymerized product of this invention offer improved mechanical capabilities that enhance the ability of the implant to withstand compressive forces, that often lead to implant failure in prior art devices. The glasses also add radiopacity to the polymerized product when it is viewed by radiographs or fluoroscopes or the like, making it much easier to confirm that the implant remains properly placed. Although preferably added to the aqueous phase of the emulsion, the glasses may in the alternative also be lodged in the polymeric phase in the polymerized product.

Bioactive ceramics or bioactive glasses, in an alternative embodiment, represent a specialized category of glasses having a unique capability to provide a means for optionally introducing other polymers, including biodegradable polymers, such as proteins. Bioglass components and their use in tissue engineering applications, such as for intervertebral disc repair are described by Ducheyne et al., *Biomaterials* 20:2287-2303 (1999); U.S. Pat. Nos. 5,964,807; 6,240,926; 6,328,990; and 6,346,123 (and the publications and patents cited therein) each of which is included herein by reference.

Granule size of the glass or bioactive glass is selected based upon the degree of vascularity of the affected tissue or on the means selected for delivery, preferably in the present invention by percutaneous injection. Generally granule size will be less than about 1000 µm in diameter. In some embodiments of the present invention it is preferred that the glass or bioactive glass granules range from about 200 µm to about 300 µm in diameter, or about 50 µm to about 100 µm, or about 10 µm to about 100 µm, or about 10 µm to about 50 µm, or even about 1 µm to about 40 µm. In an alternative embodiment these glass particles may be non-bioactive. This is achieved by increasing the $SiO_2$ content at the expense of the other oxides in the glass.

Stabilizing surfactants, that may also be included in the emulsions of the present invention, comprise two types. The first encompasses the hydrophobic, so-called low HLB surfactants which are documented in the literature, and which are described, e.g., in McCutcheon's Emulsifiers and Surfactants, McCutcheon Division, Manufacturing Confectioner Publishing Co., Glen Rock, N.J. These hydrophobic surfactants are generally soluble in hydrocarbons, and are generally insoluble in water. Those skilled in the art will recognize that these types of surfactants are those used as the emulsifying surfactants for the inverse emulsions.

The second type of stabilizing surfactants are the hydrophilic, generally water soluble surfactants. Surfactants of this type are also described in McCutcheon's, supra.

Photoinitiation of polymerization of the liquid emulsion is an embodiment of the present invention. The preferred means of photoinitiation in the present invention is by exposure to UV light for approximately 1 to 10 minutes, more typically from 2 to 5 minutes, depending on the mass and density of the emulsion being illuminated. UV light has the highest energy, and hence, is the most efficient light for most applications, although visible light may be used in the presence of selected photoinitiators. Photoinitiation allows for rapid polymerization of a significant amount of material, such as would be required to fill the nucleus pulposus in a period of a very few minutes (1 to 15 minutes) without a significant, possibly adverse increase in temperature that might cause pain or damage to surrounding tissue.

In certain embodiments of the present invention, UV light is applied transcutaneously or transdermally from an ex vivo source. While in the alternative, a sufficient amount of light (i.e., enough to initiate polymerization of the emulsion) is directed to the treatment site from an ex vivo source through fiber optics of sufficiently small diameter to fit through a minimally invasive percutaneous delivery needle. Fiber optic devices are in common use in medicine, for example, for endoscopy, and there are commercially available UV light sources with fiber optic cables for targeted delivery of the light to a small, well defined surface area ranging from about 0.1 to 1.0 $cm^2$ or more.

In yet another alternative embodiment, the organic phase may optionally contain high molecular weight polymerization initiators. Photoinitiators, such as 2-hydroxy-1-[4-(2-hydroxyethoxy)phenyl]-2-methyl-1-propane, are well known in the art of polymerization, and can be combined with a wide range of monomers, including acrylate monomers. Concentrations of the photoinitiators may range in the present invention from about 0.01% to 2.0%, and more typically from about 0.5% to 1.0%, by weight of the monomer in the emulsion.

It is also possible to use other polymerization initiators, like peroxides or redox catalysts. In an alternative embodiment, the emulsions may be polymerized using two-component systems, which consist of dual components of the emulsion differing primarily in that one component comprises the emulsion with a free radical generating initiator such as benzoyl peroxide in the range of 0.1% to 2.0%, and the second component is the same or modified emulsion containing a tertiary amine activator such as N,N diethyl-p-toluidine in the range of 0.1% to 3.0%. Upon mixing the two emulsions together, the free radical generator reacts with the activator to form free radicals, which then react with the acrylate or other unsaturated monomers to cause polymerization, which will typically be complete within 5 to 20 minutes after mixing, depending upon the concentrations of the monomers, initiator, activator, accelerator, and other compounds present in the emulsion.

The polymerized W/O emulsions, therefore, produce a viscoelastic polymerization product, obtained either by photopolymerization or by the two component system.

The dose and method of administration of the emulsion phase of the present invention will vary from subject to subject and be dependent upon such factors as the type of mammal being treated, its sex, weight, diet, concurrent medication, overall clinical condition, the particular compounds employed, the specific use for which these compounds are employed and other factors, which those skilled in the art will recognize. An amount of emulsion is administered to the patient as determined by the extent and size of the damaged tissue being regenerated or replaced. Such amounts would be known to one skilled in the art of tissue engineering. However, for intervertebral disc replacement therapy, filling the nucleus pulposus within the annulus fibrosis area would require the delivery of about 1 to 10 ml for a typical adult human to provide optimal efficacy when polymerized into gel-like form.

Therapeutically effective dosages of additive to the aqueous phase of the emulsion may be determined by either in vitro or in vivo methods, or rely upon standards known in the art. For each particular additive, individual determinations may be made to determine the optimal dosage required. The determination of the "effective dosage" levels, that is, the dosage levels necessary to achieve the desired result, will be known to those skilled in the art. The release rate of the additives may also be varied within the routine skilled in the art to determine an advantageous profile, depending on the therapeutic conditions to be treated. A typical dose of additive to the aqueous phase of the emulsion might range from about 0.001 mg/kg to about 1000 mg/kg, preferably from about 0.01 mg/kg to about 100 mg/kg, and more preferably from about 0.10 mg/kg to about 20 mg/kg. Such additives may be used alone, or in combination with other therapeutic or diagnostic agents.

The subject in need of treatment by the methods and compositions of the present invention is intended to be a mammal, preferably a human or other primate, but may also include valuable veterinary, laboratory or zoo animals in need of tissue engineering.

Non-invasive delivery methods, such as percutaneous injection are particularly preferred for the delivery of the polymerizable emulsion to the patient or to the site needing repair or replacement. Injection is the least invasive and most preferred of the non-invasive delivery methods. Accordingly, "injectable" as used in the present invention means capable of being administered, delivered or carried into the body via syringes, catheters, needles, and other means for injecting or infusing a W/O emulsion.

The injection method of the present invention can be carried out by any type of sterile needles of 18 to 26 gauge and corresponding syringes or other means for injection, such as a three-way syringe. The needles, syringes and other means for injection are commercially available from suppliers such as VWR Scientific Products (West Chester, Pa.), Beckton Dickinson, Kendal, and Baxter Healthcare. The size of the syringe and the length of the needle used will dependent on the particular injection site, based on factors such as the specific disease tissue or disorder being treated, the location and depth of the injection, and the volume and specific composition of the injectable emulsion being used. A skilled practitioner will be able to make the selection of syringe and needle based on experience and the teaching of the present invention. In the alternative, methods have been developed for the use of a delivery balloon and balloon catheter, and a polymer-injection gun in an effort to minimize invasive surgical methods, e.g., U.S. Pat. No. 5,888,220.

Of course, viscosity will be a factor in the delivery by such non-invasive methods. As is well known to those skilled in the art, high molecular weight water-soluble polymers are very viscous in solution, and concentrations in water above about 1% are often extremely viscous and difficult to pour, pump, or inject.

Other embodiments encompass the injectable emulsions disclosed herein in a ready-for-use prefilled sterile syringe; in a vial in the form of a sterile suspension; and in a two-compartment prefilled syringe, wherein one compartment contains a powder, preferably freeze-dried, and the other compartment contains a pharmaceutically acceptable carrier.

The emulsions used for tissue engineering and tissue guided regeneration must also be sterile. Sterility may be readily accomplished by conventional methods, such as filter sterilization, irradiation or treatment with gases, such as ethylene oxide, or heat, or gamma or E-beam irradiation.

In light of the foregoing information, the present invention provides a surgeon with a significant advance to treating two distinct and important groups of patients with degenerative disc disease. The first group is comprises patients in need of discectomy, a partial removal of the herniated disc to remove pressure on adjacent nerves. Although the rate of reherniation in a patient following this procedure can be as high as 15 to 38%, depending on the specifics of the particular patient's condition, until the present invention there has been no alternative treatment. The present invention, however, allows a surgeon to establish the normal function of such diseased discs by minimally invasive, injection methods.

In the second group, patients are in substantial pain due to disc degeneration, but the disc has not yet herniated, so they are not candidates for surgical correction by discectomy. The present invention, however, provides a surgeon with a minimally invasive treatment option, whereby the diseased disc can be augmented and the vertebrae again spaced apart by the introduction of the present polymerized viscoelastic product via percutaneous injection of the disclosed W/O emulsion into the center of the diseased disc. Thus, the normal and pain free function of the degenerated disc can be reestablished. When successful, the compositions and methods of the present invention, therefore, offer a tremendous advance in reversing the debilitating complications of degenerative disc disease.

The invention is particularly adapted to reconstruction of intervertebral discs, but in fact such illustrative uses can be applied to, and are intended to encompass, the any suitable tissue repair of abnormal conditions in a mammal's tissue that are caused by internal and/or external events, including, but not limited to disease, surgery, environmental exposure, injury, aging, or combinations thereof. Many terms have been used interchangeably herein, such a "generation," "regeneration," "engineering," "repair," and the like in the context of the present invention. Nevertheless, collectively the terms refer to the processes or events associated with the healing, growth, re-growth, or change of conditions of tissues, including, but not limited to, muscle tissues, connective tissues, fats, and, nerve tissues. Accordingly, the tissue defects suitable for the treatment of the present invention include, but are not limited to, defects in a mammal's heart, blood vessels, spinal column, bone, cartilage, tendon, ligament, breast, dental tissues, and the like. "Therapeutic agent," therefore, as used in the present invention, refers to any substance that provides a "therapeutic effect" when used in a "sufficient amount" to effect the treatment and reconstruction of damaged or diseased intervertebral discs.

In yet another alternative embodiment, the present invention also provides method of reconstruction and tissue generation by applying the emulsion to a substrate by a coating process, such as draw-down, spraying, painting or extrusion; or in yet another alternative, by injecting the polymerizable emulsion extra-corporeally into organs, components of organs, or tissues, prior to implant of such organs or tissues into the body, organs, or components of organs.

The invention is further defined by reference to the following specific, but nonlimiting, examples that describe in detail the preparation of exemplary injectable compositions and methods using them for tissue engineering. It will be apparent to those skilled in the art that many modifications, both to materials and methods, may be practiced without departing from the purpose or narrowing the scope of this invention.

EXAMPLES

In each of the following experiments, liquid emulsions were prepared at room temperature (ca. 23° C.) and pH7 without any buffers. The temperature for preparation of the emulsion was chosen to allow a stable system to be formed under physiological conditions that would represent those found in an operating room. Significantly higher or lower temperature could, depending upon the phase ratios and surfactants present, cause a destabilization of the emulsion. The surfactants used in the experiments were chosen to be biocompatible, but are not otherwise limiting. Accordingly, emulsion stability can be improved by optimizing the surfactant or mixture of surfactants.

Example 1

Preparation of the Basic Emulsion

In this experiment, the simplest water-in-oil (W/O) emulsion was prepared that can provide a photoinitiated, cured two-phase polymerization product. The liquid emulsion was prepared from a single organic acrylate monomer, lauryl acrylate, which was selected specifically to form a biocompatible polymer with significant viscoelastic properties. The ratio of aqueous (water-containing) phase to organic phase was chosen as 30% to represent a range of possible ratios that would provide a stable emulsion with sufficient and substantial (non-trivial amounts of) aqueous phase to enable the presence of bioactive materials or cells, if they are added.

W/O emulsion "A" was prepared by combining:
i. 101.8 g lauryl acrylate monomer (CPS Ageflex FA12P) was combined with 1.84 g BAPO photoinitiator (BAPO: bisacyl phosphine oxide) (Ciba Irgacure 819) from Ciba Specialty Chemicals, Tarrytown N.Y.; then
ii. 2.03 g PE-PEO surfactant (block co-polymer of polyethylene and polyethylene oxide from Sigma-Aldrich, Milwaukee, Wis.), HLB 4.0 (HLB: hydrophile-lipophile balance), was added to the blend prepared in step (i) to form an organic (Oil) phase; then
iii. 30.0 g deionized $H_2O$ (Water) phase was added to the components of step (ii); and
iv. all components of step (iii) were mixed (emulsified) with high sheer Cowles mixer at 4000 rpm for 25 minutes to form emulsion "A."

The mixing rate was found to be critical to formation of a stable emulsion. Emulsion "A" was stable for several hours at room temperature, but under selected conditions stability is achieved for weeks. After the emulsions became unstable, they were re-mixed as above, and were found to photoinitiate into solid viscoelastic polymerization products that cannot be distinguished visually from emulsions that were made and photoinitiated immediately.

Example 2

Addition of Bioactive Glass to the Basic Emulsion

The simple monomer and photoinitiator system of Example 1 was extended to include a bioactive glass material known to promote cell growth, see references above. This experiment was conducted to demonstrate that an aqueous dispersion of important biological components could be introduced in the liquid state and incorporated by photopolymerization into a stable 2-phase solidified polymerization product.

W/O emulsion "B" was prepared by combining:
i. 50.1 g CPS Ageflex FA12P lauryl acrylate monomer was combined with 0.89 g Irgacure 819; then
ii. 0.53 g PE-PEO surfactant, HLB 4.0 was added to 28.7 g of blend prepared in step (i) to form an organic (Oil) phase; then
iii. 1.0 g bioactive glass ceramic (MO-SCI Corp., Rolla, Mo.) and 1.0 g corn starch (Argo) was combined with 100.1 g buffered saline solution and agitated to form aqueous (Water) phase dispersion; then
iv. 10.2 g aqueous dispersion was added to the components of step (iii); and added to organic phase of step ii;
v. all components of step (iv) were mixed (emulsified) with high sheer Cowles mixer at 4000 rpm for 25 minutes, as above, to form emulsion "B."

While there was initial concern that the addition of a bioactive glass to the emulsion could destabilize the emulsion, it did not do so in the present experiment, which was important. This permits the addition of bioactive glasses to the polymerized product, which has a potential biochemical effect on any viable cells that remain in the nucleus pulposus region after implant of the emulsion and polymerization.

Example 3

Emulsion System Using Alternative Dispersant

Further extending the information provided in Examples 1 and 2 about the nature and capabilities of the emulsion system, a second dispersing agent, calcium stearate, was added to show that the invention is not limited to a single dispersant, the PE-PEO (diblock copolymer of polyethylene and polyethylene oxide) of Examples 1 and 2. In fact, the emulsion formed in Example 3 was otherwise found to be identical to that of Example 2. It is also photopolymerized successfully, although a difference was observed. The aqueous phase droplets in the emulsion of this Example 3 are of larger size than those of Example 2, demonstrating the different surfactants have different effects on the dispersed aqueous phase droplet sizes.

W/O emulsion "C" was prepared by combining:
i. 50.1 g CPS Ageflex FA12P lauryl acrylate monomer was combined, as above, with 1.01 g Irgacure 819; then
ii. 1.06 g calcium stearate was added to the components of step (i) to form an organic (Oil) phase; then
iii. 15.1 g aqueous bioglass dispersion (as used in Example 2) was added to the organic phase of step (ii) to form a pre-emulsion;
iv. the pre-emulsion components of step (iii) were mixed (emulsified) with high sheer Cowles mixer at 4000 rpm for 25 minutes, as above, to form emulsion "C."

Example 4

Photoinitiated Polymerization

Polymerization of the organic phases of emulsions A, B and C from the preceding Examples was initiated by exposure to UV light from a Honle lamp apparatus as follows:
i. 5.7 g of the mixture of the reactable monomer and photoinitiator organic phase of step (i) of Example 2 was weighed into an aluminum weighing pan and exposed under UV lamp for 2 minutes; and it formed a flexible, tacky solid polymer.
ii. 5.3 g of emulsion "A" was weighed into an aluminum weighing pan and exposed under UV lamp for 2 minutes—results shown in Table 1.
iii. 5.4 g of emulsion "B" was weighed into an aluminum weighing pan and exposed under UV lamp for 2 minutes—results shown in Table 1.
iv. 7.5 g of emulsion "B" was weighed into an aluminum weighing pan and exposed under UV lamp for 3 minutes—results shown in Table 1.
v. 10 g of emulsion "B" was weighed into a glass petri dish and exposed under UV lamp for 7 minutes—results shown in Table 1.
vi. 10 g of emulsion "B" was weighed into a glass petri dish and exposed under UV lamp for 5 minutes—results shown in Table 1.

vii. 10 g of pre-emulsion from Example 3, step (iii) was shaken by hand and weighed into a glass petri dish and exposed under UV lamp for 5 minutes—results shown in Table 1 (note that the appearance of large water bubbles in this emulsion showed that the water was poorly dispersed, and as expected the product was an unacceptable photocured gel.

viii. 10 g of emulsion "C" was weighed into a glass petri dish and exposed under UV lamp for 7 minutes—results are shown in Table 1 (note that there was no observable difference between the polymerized product of emulsion "C" cured for 5 minutes and the same emulsion "C" cured for 7 minutes, demonstrating a level of flexibility in handling the system).

ix. 10 g of emulsion "C" was weighed into a glass petri dish and exposed under UV lamp for 5 minutes—results are shown in Table 1.

Results of the UV photoinitiated polymerizations of the above samples are summarized in Table 1;

TABLE 1

| Sample No. | UV Exp. (min) | Initial State | Photoactivated State |
|---|---|---|---|
| i | 2 | Liquid, low viscosity | Solid, transparent very, tacky |
| ii | 2 | Emulsion, low viscosity | Solid, opaque, dry, tacky |
| iii | 2 | Emulsion, low viscosity | Solid, opaque, dry, tacky |
| iv | 3 | Emulsion, low viscosity | Solid, opaque, dry, tacky |
| v | 7 | Emulsion, low viscosity | Solid, opaque, dry, tacky |
| vi | 5 | Emulsion, low viscosity | Solid, opaque, dry, tacky |
| vii | 5 | Blend, low viscosity | Solid, with water bubbles |
| viii | 7 | Emulsion, low viscosity | Solid, opaque, dry, tacky |
| ix | 5 | Emulsion, low viscosity | Solid, opaque, dry, tacky |

Within the range of exposure times, all samples appeared to have fully photopolymerized. The samples that produced a solid, opaque, dry, "tacky" polymerized product were the sought after result. "Tacky" is an advantageous characteristic for a bioadhesive, which is part of the invention, especially since it is being achieved with a single, biocompatible acrylate. This effect is a contrast with the polymerized product of the 2-phase system discussed below, wherein the presence of the aqueous phase had a significant effect on viscoelasticity. While a certain level of flexibility was seen in the length of the exposure to UV light, intensity of the light and time of exposure are important to the nature of the resulting polymerized product. Too little light was found to cause slow, incomplete polymerization, whereas too much or too intense a light could be associated with the production of heat, which in excess, could damage surrounding tissue.

The viscoelasticity of the photopolymerized emulsion products were contrasted with that of the photopolymerized organic phase, as determined with a Paar Physica oscillatory rheometer (Model MCR Rheometer, Ashland, Va.) at room temperature. Table 2 shows that the viscoelasticity of the cured emulsion is significantly greater than pure lauryl acrylate, and more importantly that the resulting viscosity is of the same order of magnitude as that of the human nucleus pulposus. See, Iatridis et al. 1997 and 1999, supra.

TABLE 2

| Sample No. | Frequency (rad/sec) | G* (kPA) | delta |
|---|---|---|---|
| i | 1 | 2.9 | 35° |
| i | 100 | 8.0 | 38° |

TABLE 2-continued

| Sample No. | Frequency (rad/sec) | G* (kPA) | delta |
|---|---|---|---|
| iv | 1 | 2.0 | 48° |
| iv | 100 | 3.5 | 53° |

G* is the complex modulus; delta is the phase angle.

To better understand the significance of the results provided in Table 2, it must be understood that the nucleus pulposus is a viscoelastic material, and viscoelastic materials are those which simultaneously dissipate and store energy when a stree is applied. The specific response of a material depends upon the rate at which the molecules from which the material is comprised will reorganize over a period of time. Viscous behavior is modeled as a dashpot, in which an applied force is independent of deformation, but dependent on deformation velocity. Elastic behavior is modeled as a spring, in which in which the force is directly proportional to the deformation of the spring. The combination of springs and dashpots in parallel and in series provides various simple mechanical models, known as Voght, Maxwell and Kelvin models, for depicting the net viscoelastic behavior of a material.

There are a number of methods for evaluating viscoelastic properties. If the stress is applied in a periodic fashion with sinusoidal frequency w, then the strain, g, will also alternate sinusoidlly, but it will be shifted out of phase from the stress, s, according to the relation: s=g0(G' sin wt+G" cos wt), wherein t is time, g0 is the maximum strain amplitude, G' is the storage modulus and G" is the loss modulus. In the dynamic frequency sweep method, a small strain amplitude is applied and the frequency is systematically varied over a range typically from 1 to 100 rad/sec. The moduli are related by: G"/G'=tan d, and G*=G'+iG", wherein d is the phase angle between the stress and strain, and G* is the complex shear modulus. (See, e.g., Ferry, *Viscoelastic Properties of Polymers*, John Wiley, NY, 1980). Therefore, the components of the intervertebral disc, both annulus fibrosus and nucleus pulposus, produce viscoelastic responses that are dependent on their pathological state (See, e.g., Buckwalter et al., *Orthopaedic Basic Science*, American Academy of Orthopaedic Surgeons, Chapters 21- 22, 1999).

Example 5

Enhanced Viscosity Results from Addition of Pre-polymer

A high viscosity emulsion was formed by adding a small amount of high viscosity lauryl acrylate polymer (i.e., the pre-polymer provides higher viscosity than in the prior examples where only lauryl acrylate and bis-GMA were used) and an inert glass filler, which enhanced the viscosity of the emulsion, as well as the mechanical strength of the final, polymerized viscoelastic product. Note that bis-GMA provides covalent crosslinking to this emulsion, as opposed to self-associating, non-covalent crosslinking in the lauryl acrylates. As a result, the addition of bis-GMA provided stronger chemical forces to hold the product together in the presence of shear or compressive stresses. Photopolymerization of lauryl acrylate-containing a crosslinker, such as bis-GMA, ranging from 0.05% to 2.0% wt/wt resulted in a solid and tacky polymer.

In addition, it was shown that a free radical initiator system based on a peroxide and amine catalyst can be used, rather than necessarily always having to use a photoinitiator. Free radical initiator systems are well known in the polymer literature. See, e.g., Allcock et al., 1990, supra.

The emulsion was prepared by mixing 3 g of pre-polymerized lauryl acrylate, 2 g of silanized 2-5 μm glass powder as inert filler material, 0.5 g of 1% solution of hydroxypropyl methyl cellulose, 0.1 g of bis-GMA, 4.5 g of lauryl acrylate monomer and 0.1 g of benzoyl peroxide initiator. The emulsion was blended for 3 minutes at rpm position 10 using a VWR mini vortex mixer (Westchester, Pa.). Then 0.2 ml of tertiary amine activator (N,N diethyl p toluidine) was added to the emulsion to set off the polymerization reaction. The emulsion was immediately loaded into a plastic disposable syringe and delivered using an 18-gauge needle into an aluminum mold. The emulsion polymerized to a firm and tacky viscoelastic solid within 6 minutes after activation. Therefore, enhanced polymerization resulted from the development of a higher viscosity liquid W/O emulsion, which has the advantage of being more easily retained upon injection into the nucleus pulposus. As a result, the modified emulsion is more readily handled by a surgeon, avoiding the need for a retaining device, such as a balloon or other membrane.

Example 6

Two-component System

The emulsion of Example 5 was separated into two components that were identical, except that one contained the peroxide free radical generator, while the other contained the amine catalyst. By separating the components, it was found that the two emulsions could be maintained for longer prolonged periods of time than when they were combined, without concern of polymerization. Yet, polymerization did occur instantaneously upon mixing the two components together. See, e.g., Allcock et al., 1990, supra.

To prepare the To prepare the two-component system, first an initial base emulsion was prepared using: 20 g of pre-polymerized lauryl acrylate, 10 g of 2-5 μm silanized barium glass powder as inert filler material, 0.5 g bis-GMA, 2.5 g of a 1% solution of hydroxylpropyl methyl cellulose, and 17 g of lauryl acrylate monomer. The contents were subjected to high shear using mechanical agitation at 3500 rpm for 10 minutes. The base emulsion was then placed under 20 inches of vacuum at 25° for 2 hours, to remove any air bubbles.

The two individual components were prepared as follows. Component A was prepared by adding 0.5 g of benzoyl peroxide initiator to 25 g of the base emulsion. Component B was prepared by adding 1 ml of tertiary amine activator (N,N diethyl-p-toluidine) to 25 g of the base emulsion.

Both components were loaded into individual compartments of a dual component cartridge (System3, Auburn, Wash.). After filling, the cartridge was loaded onto a delivery gun, and a disposable static mixing tip is attached to the cartridge. The mixture was dispensed using the mixing/delivery gun into a mold of aluminum foil. The expelled material set to a firm tacky viscoelastic solid in 1 to 20 minutes. Therefore, modification of the formulation into a two-component system, in which the initiator and catalyst are separated until the desired time of mixing, provides a prolonged stable-storage capability of each of the two separate components until such time as the surgeon is ready to conduct the procedure.

Example 7

Non-invasive Delivery of Invention to Reconstruct Nucleus Pulposus of a Patient

Expanding upon Example 6, all materials were prepared with appropriate cleanliness and sterility for implantation in a living body and are tested for in vivo utility. The 2-component polymer emulsion was stored within a two component cartridge, and loaded onto a mixing/delivery gun as described above. Then the contents were dispensed through the static mixing tip, which combined the two components to initiate the polymerization reaction. The material immediately passed through the attached needle, which is inserted through the intervertebral disc and into the nucleus pulposus space before the mixing process begins. If the annulus of the disc is already herniated, the material is inserted adjacent to the herniation on inside wall of the annulus to prevent re-herniation at the injured site. Between 1 and 10 cc of material is dispensed into the nucleus cavity. The needle is removed from the patient's body and the material is completely polymerization in situ within the body within 1 to 20 minutes after delivery. Advantageously, percutaneous injected delivery of the emulsion and implantation of the polymerizable material can be achieved with by acceptably non-invasive means, but can also take place during open surgery.

Example 8

In Situ Photoinitiation of Polymerization

Expanding upon Example 7, the polymer emulsion of Example 5 was prepared as a single component system for photopolymerization by incorporating the photoinitiator 2-Hydroxy-1-[4-(2-hydroxyethoxy)phenyl]-2-methyl-1-propane (Irgacure 2959 CIBA Specialty Chemicals, Tarrytown, N.Y.) at the concentration of 0.1% by weight of the final emulsion. The emulsion blend was placed in a 10-cc syringe with an 18-gauge needle attached at the delivery end. The emulsion was delivered through the needle into a preformed cavity in a molded or machined model of an intervertebral disc. The translucent disc was exposed for 2 minutes to UV light that is channeled through a 5 mm diameter fiber optical cable. The polymer phase of the emulsion is thus initiated, and the resulting polymerized product formed a tacky viscoelastic solid, which fills the cavity in the disc. Having demonstrated the effectiveness of the photopolymerizable system, the preceding steps are also followed in vivo, whereby the viscous emulsion fills the nucleus pulposus and the polymerized product forms in situ, becoming a permanent implant, replacing and reconstructing the damaged or degenerating nucleus pulposus of a patient.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

We claim:

1. A method of preparing a nontoxic, viscoelastic material for tissue engineering, wherein the viscoelastic material comprises a polymerized emulsion having two discrete organic and aqueous phases, the method comprising:
   a) preparing a nontoxic, inverse ("water-in-oil") fluid emulsion comprising two discrete phases:
      i) a continuous hydrophobic organic ("oil") phase, comprising one or more reactive, ethylenically unsaturated, polymerizable acrylate monomers, and at least one activator-controlled polymerization initiator; and
      ii) a discontinuous aqueous ("water") phase comprising water,
   wherein the aqueous phase is present in the emulsion in an amount of about 0.5% to about 90% weight/weight of the organic phase; and
   b) polymerizing the fluid emulsion in situ to form the viscoelastic material, wherein the viscoelastic material comprises:
      i) a continuous hydrophobic organic phase comprised of polymerized ethylenically unsaturated acrylate monomers;
      ii) a discontinuous aqueous ("water") phase comprising water.

2. The method of claim 1, wherein at least one of the reactive, ethylenically unsaturated, polymerizable acrylate monomers, is selected from the group consisting of methyl acrylate; methyl methacrylate; ethyl acrylate; ethyl methacrylate; stearyl acrylate and methacrylate; lauryl acrylate and methacrylate; ethoxylated and/or propoxylated acrylates and methacrylates; alkoxylated acrylates and methacrylates; allyl acrylates and methacrylates; tetrahydrofurfuryl methacrylate; isodecyl acrylate or methacrylate; octyldecyl acrylate and methacrylate; phenoxyethyl acrylate and methacrylate; glycidyl acrylate and methacrylate; isobornyl acrylate; caprolactone acrylate; ethoxylated nonyl phenol acrylates and methacrylates; propylene glycol acrylate and methacrylate; alkoxylated nonyl phenol acrylates and methacrylates; alkoxylated diol diacrylates; alkoxylated bisphenol diacrylates; ethylene glycol diacrylate; butylene glycoldiacrylate and dimethacrylate; butanediol diacrylate and dimethacrylate; neopentylglycol diacrylate and dimethacrylate; polyethyleneglycol diacrylate and dimethacrylate; ethoxylated bisphenol diacrylates; saturated and unsaturated (C36) dimer diol diacrylates; polyethyleneglycol diacrylate and dimethacrylate; polybutadiene diacrylate and dimethacrylate; polybutadiene urethane diacrylate; triethylene glycol dimethacrylate; acrylamide and methacrylamide.

3. The method of claim 1, further comprising pre-polymerizing at least one of the reactive, ethylenically unsaturated, polymerizable acrylate monomers.

4. The method of claim 3, wherein the pre-polymerized monomer is lauryl acrylate, and it replaces a fraction of the monomer in the organic phase of the emulsion.

5. The method of claim 1, wherein the aqueous phase of the fluid emulsion further comprises at least one additive selected from the group consisting of stabilizers, stabilizing salts, diluents, solubilizers, lubricants, suspending agents, encapsulating materials, solvents, thickeners, dispersants, buffers, anti-oxidants, preservatives, low molecular weight peptides, proteins immunoglobulins, hydrophilic polymers, amino acids, monosaccharides, disaccharides, carbohydrates, cellulose or its derivatives, glucose, mannose, dextrines, chelating agents, sugar alcohols, counter-ions, and non-ionic surfactants.

6. The method of claim 1, wherein the polymerization of the fluid emulsion is initiated by thermal, chemical or photo-initiation means.

7. The method of claim 1, wherein the polymerization initiator is a photoinitiator.

8. The method of claim 6, wherein the photoinitiation means comprises exposing the fluid emulsion in situ to electromagnetic radiation.

9. The method of claim 1, wherein the polymerization initiator is a chemical initiator.

10. The method of claim 1, wherein the fluid emulsion further comprises particles, solutions or dispersions of at least one inert, bioactive or biological material.

11. The method of claim 7, wherein the photoinitiator is 2-hydroxy-1-[4-(2-hydroxyethoxyphenyl]-2-methyl-1-propane or bisacyl phosphine oxide.

12. The method of claim 8, wherein the electromagnetic radiation is ultraviolet light, visible light, infrared light, or microwaves.

13. The method of claim 9, wherein the chemical initiator is a peroxide or a redox catalyst.

14. The method of claim 9, wherein the chemical initiator is a combination of benzoyl peroxide and a tertiary amine.

15. The method of claim 10, wherein the inert, bioactive or biological material is selected from the group consisting of biological cells or cell fragments, tissue fragments derived from in vitro or in vivo cell culture, biological cell or tissue growth factors, agents to facilitate cell delivery or cell growth and their delivery, antibodies, antibody fragments, hormones, cell targeting moieties, inert ceramics, inert glasses, bioactive ceramics and bioactive glasses.

16. The method of claim 1, wherein the aqueous phase of the fluid emulsion comprises droplets having a size of $\geq 1$ micron.

17. The method of claim 1, wherein the fluid emulsion further comprises an emulsifier.

18. The method of claim 17, wherein the emulsifier is present in an amount of about 0.1% to about 5.0% by weight of the emulsion.

19. The method of claim 1, wherein the aqueous phase of the fluid emulsion further comprises at least one polymer selected from the group consisting of polyelectrolytes, polysaccharides, proteins, proteoglycans, nucleic acids, hydroxyethylcellulose, and carboxymethylcellulose.

20. The method of claim 1, wherein the fluid emulsion further comprises at least one filler selected from the group consisting of radio-opacifiers, polymeric microspheres, glass, sugar crystals, and proteins.

21. The method of claim 1, wherein the fluid emulsion further comprises at least one medicament.

22. The method of claim 21, wherein the medicament is an anesthetic.

23. The method of claim 22, wherein the anesthetic is selected from the group consisting of lidocaine, xylocaine, novocaine, benzocaine, prilocaine, ripvacaine, and propofol.

24. The method of claim 21, wherein the medicament is selected from the group consisting of antibiotics, steroids, fibronectins, cytokines, growth factors, analgesics, antiseptics, glucagons, polynucleotides, proteins, peptides, cell attachment mediators, and osteoinductive substances.

25. The method of claim 24, wherein the polynucleotide is cDNA or DNA.

26. The method of claim 21, wherein the medicament is selected from the group consisting of alpha-, beta, or gamma-interferon, erythropoietin, calcitonin, heparin, interleukin-1, interleukin-2, filgrastim, HGH, luteinizing hormone, atrial natriuretic factor, Factor VIII, Factor IX, follicle-stimulating hormone, acyclovir, cephradine, malfalen, procaine, ephedrine, adriomycin, daunomycin, plumbagin, atropine, quanine, digoxin, quinidine, cephalothin, proline, cis-hydroxy-L-proline, penicillin V, aspirin, ibuprofen, nicotinic acid, chemodeoxycholic acid, chlorambucil, bone morphogenic proteins, epidermal growth factor, fibroblast growth factor, platelet-derived growth factor, insulin-like growth factor, and transforming growth factor-beta.

27. The emulsion of claim 21, further comprising at least one carrier selected from the group consisting of saline, starch, hydrogel, polyvinylpyrrolidone, polysaccharide, hyaluronic acid ester, and plasma.

28. A method for preparing a nontoxic, viscoelastic material for tissue engineering, wherein the viscoelastic material comprises a polymerized emulsion having two discrete organic and aqueous phases, the method comprising:
   a) preparing a nontoxic, inverse ("water-in-oil") fluid emulsion comprising two discrete phases: i) a continuous hydrophobic organic ("oil") phase, comprising one or more reactive, ethylenically unsaturated, polymerizable acrylate monomers, and a peroxide free radical generator; and ii) a discontinuous aqueous ("water") phase, wherein the aqueous phase is present in an amount of about 0.5% to about 90% weight/weight of the organic phase;
   b) preparing a nontoxic, inverse ("water-in-oil") fluid emulsion comprising two discrete phases: i) a continuous hydrophobic organic ("oil") phase, comprising one or more reactive, ethylenically unsaturated, polymerizable acrylate monomers, and an amine catalyst; and ii) a discontinuous aqueous ("water") phase, wherein the aqueous phase is present in an amount of about 0.5% to about 90% weight/weight of the organic phase; and
   c) combining the emulsions of steps a) and b) to initiate polymerization to form the viscoelastic material comprising of:
      i) a continuous hydrophobic organic phase comprised of polymerized ethylenically unsaturated acrylate monomers; and
      ii) a discontinuous aqueous ("water") phase comprising water.

29. The method of claim 28, wherein the peroxide free radical generator is benzoyl peroxide.

30. The method of claim 28, wherein the amine catalyst is a tertiary amine catalyst.

31. The method of claim 30, wherein the tertiary amine catalyst is N,N-diethyl-p-toluidine.

32. The method of claim 1, wherein the fluid emulsion further comprises inert glass.

* * * * *